United States Patent [19]

Koezuka et al.

[11] Patent Number: 5,356,793
[45] Date of Patent: Oct. 18, 1994

[54] METHOD FOR TESTING THE SENSITIVITY OF ANTICANCER DRUG

[75] Inventors: Masahiro Koezuka, Nara; Naohito Kondo, Osaka; Sachiko Oda, Osaka; Hisayuki Kobayashi, Osaka; Masayuki Yasutomi, Osaka, all of Japan

[73] Assignee: Nitta Gelatin Inc., Osaka, Japan

[21] Appl. No.: 649,526

[22] Filed: Feb. 1, 1991

[30] Foreign Application Priority Data

Mar. 15, 1990 [JP] Japan ................................. 2-66328
Oct. 3, 1990 [JP] Japan ................................ 2-267343

[51] Int. Cl.$^5$ .................... C12M 1/00; C12M 3/00; C12N 5/06; C12N 5/00
[52] U.S. Cl. ............................... 435/32; 435/240.1; 435/240.2; 435/240.23; 435/240.25; 435/808; 435/284; 364/924.2; 382/6; 382/10; 382/25
[58] Field of Search ........... 435/240.2, 240.23, 240.25, 435/240.243, 240.1, 808, 4, 29, 32, 284; 364/924.2, 924; 382/6, 10, 25

[56] References Cited

U.S. PATENT DOCUMENTS 3,493,772  2/1970  Daughters et al. ................. 250/222
4,637,053  1/1987  Schalkowsky ...................... 435/291

OTHER PUBLICATIONS

Koezuka et al, "Tissue Culture Research Communications", vol. 6, No. 1, Jun. 1987.
Arii T., et al., J Electron Microscopy vol. 36, No. 4, pp. 177-195 (1987).
Kawamura K., et al Proc Japan Acad 62 Ser B. (1986).
Enami J., et al. Dokkyo J of Medical Sciences vol. 12, pp. 25-30 (1985).
Bodin et al, Methods in Laboratory Investigation "Study of Living Single Cells in Culture: Automated Recognition of Cell Behavior" vol. 39, No. 1, pp. 137-143, 1988.
Jaggi et al, The Design and Development of an Optical Scanner for Cell Biology, 27-30 Sep. 1985, pp. 980-985.
Koezuka et al Biosis #38091394 Biological Abstracts (1990).
Blystone et al Biosis #40020455 Biological Abstracts (1991).

*Primary Examiner*—Michael G. Wityshyn
*Assistant Examiner*—Jane A. Williams
*Attorney, Agent, or Firm*—Lowe, Price, LeBlanc & Becker

[57] ABSTRACT

The present invention relates to a method of testing the sensitivity of cancer drugs with cancer cells cultured in vitro. Cancer cells are cultured in a collagen gel substrate. A wide variety of human cancer cell types readily proliferate in the collagen gel substrate, however, fibroblast cells proliferate as well. The measurement of the growth of the cancer cells is hindered by the presence of the fibroblast cells. The present invention solves this problem by counting the number of colonies with an image processor which selectively extracts the image signals of cancer cells and their colonies. In a second embodiment, the growth of cancer cells is determined by measuring the volume of colonies with the image signals of cancer cells and their colonies selectively extracted. The results can be obtained effectively within a short period of time.

6 Claims, 11 Drawing Sheets

METHOD FOR TESTING THE SENSITIVITY OF ANTICANCER DRUG

BACKGROUND OF THE INVENTION

The present invention relates to a testing method for sensitivity of anticancer drugs and, in detail, relates to a method in which the sensitivity of cancer cells to anticancer drugs is tested with cancer cells cultured in vitro.

There have been known the following methods for determining the therapeutic efficacy of anticancer drugs, or for the drug-sensitivity test: a clinical testing method in which anticancer drugs are dosed to cancer patients and the change in cancer tissue is examined by diagnostic examination; an in vivo (animal) testing method in which anticancer drugs are dosed to animals to whom human cancer tissue is transplanted; a cell culture testing method in which cancer cells are taken from cancer patients, brought in contact with anticancer drugs and then cultured by using an adequate substrate, or the cells are brought in contact with the drug while cultivating, and after a definite period of time, the growth of cancer cells is measured; and other methods.

It is as usual that after confirmation of the anticancer efficacy of newly developed anticancer drugs by using the cell culture or in vivo-testing methods, the drugs are tested clinically to confirm the efficacy in a final stage, because they can not be applied to the clinical testing method from the first stage of their development. The in vivo-testing method suffers disadvantages of difficulties in controlling animals for experiments such as nude mice etc. and low success rate in the transplantation of human cancer cells, and also requires a long period of time before obtaining experimental results. In contrast, a cell culture testing method has advantages that it is performed by using a relatively simple equipment and by a relatively simple procedure and provides the experimental results in a short period of time. Therefore, an anticancer drug sensitivity test by a cell culture testing method plays a very important role in the development of new anticancer drugs.

Hitherto, as a typical cell culture testing method, a method which is called as the HTCA (Human Tumor Clonogenic Assay) method has been known. According to the method, a single cell suspension is prepared from cancer tissue obtained from a living body and brought in contact with an anticancer drug, and the cancer cells are then cultured in a soft agar substrate. Subsequently, the number of the cancer cell colonies formed after cultivating for a definite period of time is counted to evaluate the inhibition rate on the colony formation by the anticancer drug and thereby the anticancer drug sensitivity is tested. The counting of colonies is performed with eye measurement or by using a colony counter. As alternatives, there are methods in which cells are cultured by using a monolayer culture technique followed by evaluating the efficacy of anticancer drugs against cancer cells using an isotope method and a DNA-measuring method and others.

However, the HTCA method which is the most typical anticancer drug sensitivity testing method in the cell culture methods has the following problems.

First, although the cell culture method using soft agar substrata has an advantage of depressing proliferation of fibroblasts, it requires a large number of cells for culture because of the low colony formation rate of cancer cells. Therefore, the number of tests being carried out with the limited quantity of obtained cells is smaller. Second, there is a problem that the kinds of cancer cells capable of being cultured are limited. That is, the cancer cells variously differ in kind and character due to a tissue difference etc. in a diseased part so that among these variously different kinds of cancer cells only a few kinds of cells can be cultured in a soft agar substrate.

The present inventors, therefore, examined a new anti-cancer drug-sensitivity test, in which a collagen gel substrate was used in place of a soft agar substrate, in a primary culture system using human cancer cells. As a result, we found that even the human cancer cells which did not proliferate in a soft agar substrate were able to proliferate steadily in collagen gel substrate (refer to Koezuka et. al., "Tissue Culture Research Communications", Vol. 6, No. 1, 1987). From the results, the collagen gel culture method made it possible for the cell culture testing method to greatly spread the range of adaptability. Furthermore, the method has been found to have advantages of that the number of cells required for culture is small because cancer cells are proliferated more effectively in collagen gel than in soft agar etc., and that the test results can be obtained effectively within a short period of time.

Generally, when collagen gels are used as substrata, the DNA of cells proliferated in collagen gels is measured for determination of the growth of cancer cells.

However, when cancer cells are cultured in a collagen gel substrate, the collagen gel culture creates a problem that fibroblasts which are contained in cancer tissues also proliferate together with the cancer cells, depending on the kind of the cancer tissue. Since the fibroblasts also possess DNA similarly to the cancer cells, the method for measuring the growth of cancer cells by the above-mentioned quantitative determination of DNA can not be used. Therefore, in such a case the formed cancer cell colonies have to be counted by eye measurement or by means of a colony counter. However, when the measurement is carried out by eye measurement using a stereoscopic microscope, selective counting of the cultured cancer cells alone requires a great deal of labor, and the measurement varies from observer to observer, resulting in inaccurate results. It is also actually impossible to distinguish exactly between the cultured cancer cells and fibroblasts by means of a conventional colony counter. In most human cancer tissues obtained from a surgery material, fibroblasts and cancer cells proliferate simultaneously in collagen gel substrata, and hence it is very difficult to examine the sensitivity of anticancer drugs against human cancer cells cultured in the substrate unless both the fibroblasts and cancer cells are separated. Although several techniques such as the cis-hydroxyproline(Oxyprolin) method, the D-valine method, the citrulline method, and the like have hitherto been proposed as methods for depressing the proliferation of fibroblasts without depressing proliferation of cancer cells, none of these techniques is practically useful because they are effective for only a few, limited kinds of fibroblast.

SUMMARY OF THE INVENTION

An object of the present invention is to provide a testing method for testing the sensitivity of anticancer drugs, which has not only the advantage of collagen gel substrate capable of cultivating cancer cells effectively, but also capability of simply and accurately measuring the growth of cancer cells alone, even if the fibroblast proliferation simultaneously occurs that is up to present a defect of the collagen gel substrate.

To solve said object, the present invention provides a testing method for testing the sensitivity of anticancer drugs, wherein cancer cells are proliferated by using a collagen gel as a substrate and an image processor is used as a means for measuring the growth of cancer cells. Thus, image signals of the cancer cells and their colonies are selectively extracted from those of a sample obtained with imaging and the growth of cancer cells is determined with the thus-obtained image information of the cells and colonies to assay the anticancer drug sensitivity.

According to one embodiment in the present invention, the growth of cancer cells is determined by counting the number of colonies with the image signals of cancer cells and their colonies selectively extracted.

According to another embodiment in the present invention, the growth of cancer cells is determined by measuring the volume of colonies with the image signals of cancer cells and their colonies selectively extracted.

The collagen used as a substrate may be capable of gelation, and type I collagen which shows high gel strength is further preferred. Additionally, since an optical measurement is being carried out, it is preferable that the collagen used in the present invention is such that is exhibits transparency for light having the wavelength used for the measurement, and further that it has an optically uniform character in the gel form. Furthermore, collagen which does not cause any optical quality-change due to time-passage during culturing is desired.

Also, the process in which cancer cells are cultured in a substrate composed of collagen gel is carried out according to hitherto-known, various kinds of tissue-culture methods using collagen gel. The time when an anticancer drug is brought in contact with cancer cells may be properly set, for example, it may be just before inoculating cancer cells taken from a patient(primary cancer cells) into a collagen gel substrate; before inoculating cells treated with subculture of the primary cancer cells into the substrate; immediately after inoculating them into the substrate; or after several days' cultivation of cells inoculated. There is no special limitation about the time.

An image processor is used as a means which measures a change in the growth of cancer cells. The image processor is connected with an optical instrument such as a microscope etc. and image signals obtained thereof are converted into numerical image information followed by arithmetic processing and, thus the processor is used in order to obtain clear and acurate information of an object. Thus, the processor is equipped with an image processing mechanism such as a microcomputer, etc.; a memory mechanism for the image derived from a fixed disk device, etc.; and an outputting mechanism such as a monitor television or a video printer for outputting the image information processed.

The microscope used may be similar to a microscope which has hitherto been used for measuring cancer cells with eye measurement. Measurement performance and measurement accuracy can be elevated by properly selecting the conditions such as the magnification of a microscope that is largeness of a visible scope, depth of a focus, distance of a subject, an equipping structure of culturing vessels, and an illuminating apparatus etc. The microscope may be equipped with an inputting device such as a TV camera in order to input the sample image signals into the image processor.

Setting of a culture sample at an observing position of a microscope can be performed by hand, but if a continuous transfer mechanism which is able to send a culture sample continuously to the observing position or to take out the sample is equipped, an attempt to raise efficiency of measurement may be achieved.

In the present invention, a TV camera of the image processor receives gray images of a cultured sample. For the sample images received, there is a case where only the images of cancer cells and their colonies(-hereinafter referred to as "cancer cells") exist and a case where the images of those and images of the above-mentioned fibroblasts exist as a mixture. The image processor undergoes processing for removing unnecessary images such as those of fibroblasts etc. other than the cancer cells from the sample images. To separate the images of cancer cells from the other unnecessary images and remove the latter images, a function for separating the gray levels and shapes in the image processor is employed. The cancer cells form a solid image having a certain degree of size as well as a profile and a gray level by that a large number of cells gather together, that is a colony, whereas the fibroblasts take a fine fibrous shape or a twig shape as suggested by the name. Therefore, the cancer cells and fibroblasts can be distinctly distinguished by the shape difference as well by differences in the gray levels of images. Thus, the image processor recognizes as cancer cells only the images in which the shape, area, gray level, and color difference etc. fulfills definite conditions, and also recognizes the images, which does not fulfill said condition, as unnecessary images of fibroblasts etc. and thus, the images other than the images of cancer cells are removed and the remaining cancer cell images can be taken out. Then, when the shapes of individual images being shown in the cancer cell images undergo arithmetic processing and are evaluated, a change in the growth of cancer cells, that is a proliferating extent, can be measured.

In order to evaluate the sensitivity of anticancer drugs, for example, a pair of cancer cells, one of which is brought in contact with an anticancer drug or with different anticancer drugs of two or more kinds and the other of which is not brought in contact with any anticancer drug as a control experiment, are cultured under identical conditions, and change in the growth of cancer cells measured with said image processor is compared.

To determine a growth extent of cancer cells with the images of cancer cells selectively extracted, as described above, there are, for example, the following two kinds of procedure. One is to count the number of colonies in the images of cancer cells. The other is to measure the volume of colonies in the images of cancer cells.

According to the first procedure, for example, the number of colonies obtained by culturing cancer cells which have been brought in contact with an anticancer drug and that obtained by culturing cancer cells' without the contact (control experiment) are determined by automatic counting for comparison.

According to the other procedure, for example, the volume of colonies obtained by culturing cancer cells which have been brought in contact with an anticancer drug and that obtained by culturing cancer cells without the contact (control experiment) are derived for comparison. Here, the derivation of the volume is, for example, carried out as the undermentioned, but it is not limited within it.

With culturing of cancer cells in the collagen gel substrate, the kind of cancer cells being cultured increases the application region of the cell culture testing method enlarges, and also the growth of cancer cells proceeds smoothly and the test results can be obtained surely and promptly.

By that the amount of colonies formed with cancer cells is measured and analysed by means of an image processor, the effect of fibroblasts which proliferate together with cancer cells can be eliminated. That is, in an image of a cultured sample, the cancer cell image shows a block shape and a dark image, while the fibroblast shows a light image of a fine fibrous shape, so that the cancer cell and fibroblast are distinctly different in the shape and gray level. In the image processor, only the images having a shape and a grey level of definite conditions can be taken out from inputted images, so that the images of cancer cells and those of fibroblasts are separated to take only the images of cancer cells. Also, besides the fibroblasts, the images of unnecessary objects having a grey level and a profile different from those of cancer cells, can be separated from the images of cancer cells. When the amount of colonies being formed with cancer cells is measured with the cancer cell images taken out, a change in the growth of only the cancer cells which do not involve the fibroblasts can be measured.

The measurement by an image processor, for example, when it is compared with that by the nude eye under a microscope, is capable of measuring a complex amount more effectively and precisely and within a far shorter period of time, and also the measurement can be carried out under definite conditions avoiding scattering of results and possibility of erroneous measurement which results from a different skill etc. of measuring workers, so that the test results are stable.

Additionally, since the present method is a nondestructive method, the measurement of an identical sample can be carried out with passage of time and, in a case of that a change in amount of the object, that is cancer cells, is measured, such measurement accuracy as that can not be obtained from a destructive method may be easily realized. Furthermore, the process which is necessary for analyses may be automated inside the image processor and, if it is linked to a continuous measuring mechanism, the time and labor necessary for measurement can be reduced and rationalized.

If measurement of a growth extent of cancer cells is carried out by number-counting of colonies with the cancer cell images selectively extracted, precise results were obtained with an inexpensive image processor only in cases wherein the colonies do not come in contact with one another.

Also, if measurement of a growth extent of cancer cells is carried out by volume measurement of colonies with the cancer cell images selectively extracted, when colonies came into contact with one another or overlapped, more precise results were obtained compared with the above number-counting.

DESCRIPTION OF THE PREFERRED EMBODIMENTS

Figure 1:
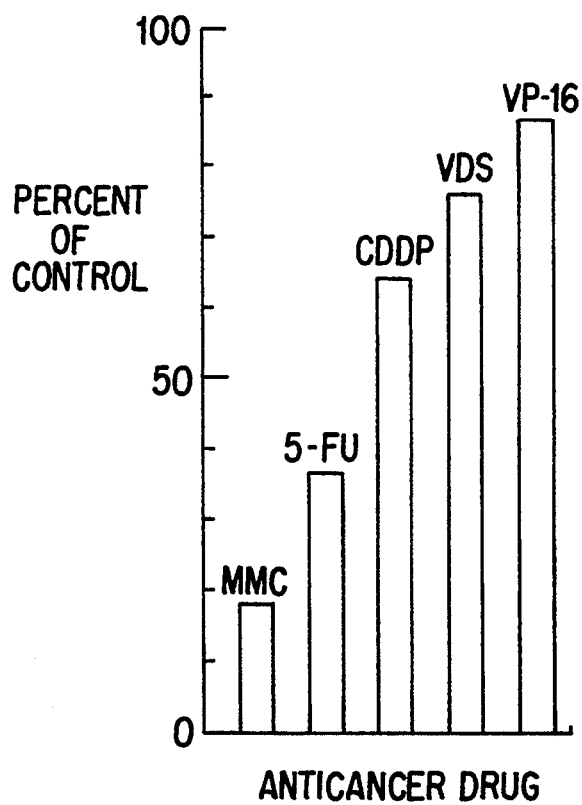
FIG. 1 is a graphic diagram which shows results obtained from the measurement of sensitivities of anticancer drugs in the examples of the present invention.

The examples of the present invention are explained in detail, but this invention is not limited within the undermentioned examples.

EXPERIMENT 1

Comparison of Collagen Gel Culture With Other Kinds of Culture

Initially, it was confirmed by experiments that the collagen gel substrate employed in this invention was superior to the so far known soft agar gel substrates for the culture of human cancer cells.

Table 1 presented below shows the results obtained from the culture of various kinds of human cancer cells in collagen gel substrate and so far known soft agar substrate.

The culture method used in the so far-known HTCA method was used for the soft agar substrate in the table. Upon observation of the cultured samples after culturing, if the number of colonies of cancer cells exceeded 20, the culture was evaluated as successful. The numerical values in each column of the table show the number of success in the culture versus the number of total experiments. The number of cells inoculated were $5 \times 10^4$ for 1 ml of collagen gel substrate and $5 \times 10^5$ for 1 ml of soft agar substrate.

TABLE 1

| Kinds of cancer cells | Collagen gel substrate | Soft agar substrate |
|---|---|---|
| Colon cancer-1 | 5/5 | 0/5 |
| Colon cancer-2 | 5/5 | 4/5 |
| Colon cancer-3 | 1/5 | 0/5 |
| Rectal cancer-1 | 5/5 | 2/5 |
| Lung cancer-1 | 5/5 | 0/5 |
| Lung cancer-2 | 0/1 | 1/1 |
| Total | 21/26 | 7/26 |

As seen from said results, it was proved that, when a collagen gel substrate is used, many more kinds of cancer cells were successfully cultured as compared to when a soft agar substrate is used.

EXAMPLE 1

According to the undermentioned procedure, the anticancer drug sensitivity tests in the present invention were carried out to compare the effects of plural anticancer drugs.

Culture of Cancer Cells

The culture of cancer cells being supplied to image processing was carried out.

The cancer cells used were human cancer cells separated from nude mouse-xenografted human colon cancer by a stepwise enzyme-treatment using collagenase and pronase. The obtained cells were embedded in collagen gels and cultured.

The embedding was carried out as follows: to 8 volumes of Cellmatrix Type I-A (0.3% acid-soluble collagen solution, made by Nitta Gelatin Inc., Japan) were added 1 volume of 10 times concentrated Ham's F12 medium(not containing $NaHCO_3$), 1 volume of a reconstitution buffer(aqueous 50 mM sodium hydroxide solution containing 260 mM of $NaHCO_3$ and 200 mM of HEPES), and 1 volume of FBS(fetal bovine serum), and to the mixture thus-obtained were added and mixed well the human cancer cells which were obtained from said enzyme-treatment, and the mixture thus-prepared was kept in ice. One ml of the collagen-cell mixture solution was pipetted into each Petri dish of 35 mm diameter. The cell number was $5 \times 10^4$ cells/ml. This mixture solution was then warmed to 37° C. in a carbon dioxide incubator to form collagen gel substrata containing the human cancer cells.

The resulting collagen gel substrata were overlayed with 1 ml of a culture medium containing each of anticancer drugs and allowed to stand for 24 hours at 37° C. in the carbon dioxide incubator to bring the cells in contact with drugs. Hereafter, the medium which contained drugs was removed by suction, and 2 ml of a culture medium which does not contain anticancer drugs were added and shaken in the carbon dioxide incubator to wash the collagen gel substrata. This washing was repeated 10 times at 10 minutes intervals to remove drugs from the substrata. In the control experiment a culture medium which does not contain anticancer drugs is used and the contact of human cancer cells with anticancer drugs is not carried out.

Next, 2 ml of a culture medium was added and cancer cells were cultured for 10 days at 37° C. in the carbon dioxide incubator. The culture medium was changed at 1 to 2 day intervals. After culturing, each collagen gel substrate containing cells was fixed by using 10% aqueous formalin to prepare the samples.

The culture medium used in the above procedure was composed of DME, 10% of FBS, Insulin (1 μg/ml), and a EGF culture medium (10 ng/ml); where the DME is Dulbecco's Modified Eagle's culture medium (made by Nissui Seiyaku Co.), FBS is Fetal Bovine Serum (made by Gibuko Co.), Insulin is insulin (from Sigma Co.), and EGF is Epidermal Growth Factor (made by Collaborative Co.).

Anticancer drugs used herein were the following five kinds: mitomycin (MMC made by Kyowa Hakko Kogyo Co., Ltd., Tokyo), 5-fluorouracil (5-FU made by Kyowa Hakko Kogyo Co., Ltd.), Vindecine sulfate (VDS made by Shionogi Pharmaceutical Co., Ltd., Tokyo), Etoposide (VP-16 made by Nippon Kayaku Co., Ltd.), and Cisplatin (CDDP made by Bristol-Myers Co., Ltd., Tokyo).

The concentration for use of each anticancer drug which was brought in contact with cells was equivalent to one-tenth of the highest concentration achievable in blood among various concentrations of the drug for clinical use(concentration in tumor tissue). They were 0.1 μg/ml for MMC, 1.0 μg/ml for 5-FU, 0.005 μg/ml for VDS, 0.1 μg/ml for VP-16, and 0.2 μg/ml for CDDP.

Image Processing

Both the pictures of the colonies of the human cancer cells, which were proliferated in collagen gel substrata, and fibroblasts, which were proliferated simultaneously with the cancer cells, in the fixed samples prepared as mentioned above, were taken with a TV camera through a stereoscopic microscope, whereby the images obtained were inputted as image signals into an image processor (LUZEX III U, made by Nikon Co., Ltd.)

Specifications of the image processor are as follows.
Control processor: Intel 80386/7 32 bits processor
Memory unit: 40 megabytes fixed disk drive
Image processing circuit: image area and density, maximum $1024 \times 1024$ pixel $\times (8+1)$ bit, image array processor
Image inputting device: TV camera, Chalnicon camera tube, optical microscope
Image outputting device: digital/analog RGB monitor, video printer The image signals inputted into the image processor were digitized into picture elements and the concentrations corresponding to each element of the image were converted into numerals and then, taking the images of colonies of cancer cells and those of fibroblasts as the objects, processing to separate them from the original images was carried out. The processing for separating the object images enhanced a feature in the gray level of the objects by a logical operation. For this operation, a high-frequency component extracting operation, a gray level-classifying operation, and a noise removal were used in combination. Only the images of the objects were extracted from the obtained, enhanced images, according to a definite standard value relating to the gray level. At this stage, the numbers of colonies due to only human cancer cells were counted with a difference in the gray levels or a difference in a changing rate of the gray levels. In the images after the image processing being carried out, the colonies of cancer cells of the present object are only enhanced and the unnecessary images of fibroblasts etc. has been removed, so that counting the number of colonies is easy.

Examination of Measurement Results Obtained by Image Processing

As described above, from the images after the image processing being carried out, the measurement results of colonies of only human cancer cells are compared with the results which are obtained from similar measurements without the image processing.

When a formalin-fixed sample which has not been brought in contact with an anticancer drug is seen with a stereoscopic microscope, there exist in a mixture the colonies of cancer cells having a sphere shape and the fibroblasts being formed in a bipolar linear shape.

Under these conditions, when only colonies of a sphere shape, that are the colonies of cancer cells, were carefully and with time-taking measured with counting by the naked eye, the number were 52 pieces per 1.4 square millimeters (one visual field). The counting was carried out under a condition of a high extent of enlargement by a stereoscopic microscope.

When a picture-taken image of the same sample was counted in a stage previous to the image processing by a colony counter which is usually employed, the colony number was 1024 pieces per 1.4 square millimeters, so that precise counting of colonies of cancer cells was not possible by an influence of fibroblasts.

Next, the counting result of colony number for the image in a stage of that said image processing (a high frequency component extracting operation and a gray level-classifying operation) which had already been carried out was 51 pieces per 1.4 square millimeter, which is almost the same result as the counting-measurement result by said naked eye. Therefore, it was proved that the counting of the colony number resulting from the image processing has sufficient accuracy. Also, the colony number-counting for the image in a stage of that said image processing was already carried out was far simpler than the counting of only the cancer cell colonies in a fibroblasts etc.-coexisting mixture.

Result of Counting of Colony Numbers After Image Processing

Table 2 below-presented shows results of image processing as described above followed by counting the colony numbers concerning samples which were brought in contact with anticancer drugs. In order to raise the measurement accuracy the counting of colony numbers was carried out with a low extent of enlargement (one visual field of 2.8 mm × 2.8 mm).

TABLE 2

| Anticancer drug | Colony number/2.8 mm × 2.8 mm |
|---|---|
| (—) | 206 |
| MMC | 37 |
| 5-FU | 74 |
| VP-16 | 181 |
| VDS | 159 |
| CDDP | 113 |

In Table 2, the symbol (-) indicates a case where any anticancer drug is not used (a control experiment) and, the anticancer drug for the sample having a smaller number of colonies in comparison with this control, that is the sample in which the growth of cancer cells has been depressed, indicates higher sensitivity.

EXPERIMENT 2

Comparison with Previous Method

To confirm the reliability of the method of the example in this invention for an anticancer drug sensitivity test, the obtained results were compared with the measurement results from the nude mouse method which at present has been recognized as a method showing the best clinical correlation in anti tumor effect.

First, from the counting results of the colony numbers obtained from said example, the percentages of the numbers of colonies formed when treated with each anticancer drug against those when untreated (control experiment) were derived with calculation as "percent of control". Results are shown as graphs in FIG. 1.

Next, the anticancer drug sensitivity test using nude mice (Example for comparison 1) was carried out as undermentioned. The nude mouse-xenografted human colon cancer, which was used in the forementioned "Culture of cancer cells", was minced into fragments of approximately 2 mm in cubic size and, subsequently, transplanted subcutaneously into nude mice. Then, when the estimated weight of the tumors(cancers) reached approximately 100 mg, each of 3 mg/kg of said MMC, 50 mg/kg of 5-FU, 25 mg/kg of VP-16, 5 mg/kg of CDDP, and 3 mg/kg of VDS was injected 4 times weekly into the abdominal cavity of 5 nude mice in each group and an, additional one group was served as controls for which the anticancer drug is not injected. The estimated weights of tumors were calculated by measuring the length (L mm) and width (W mm) of the tumors and using a formula $L \times W^2/2$. Then, at one week later than the final injection, the estimated weights of tumors were again measured, and the percentages of the mean tumor weights in the case of that treatment with each drug was carried out against those in the case untreated with a drug (control) were calculated similarly as "percent of control". The results are illustrated in FIG. 2.

Figure 2:
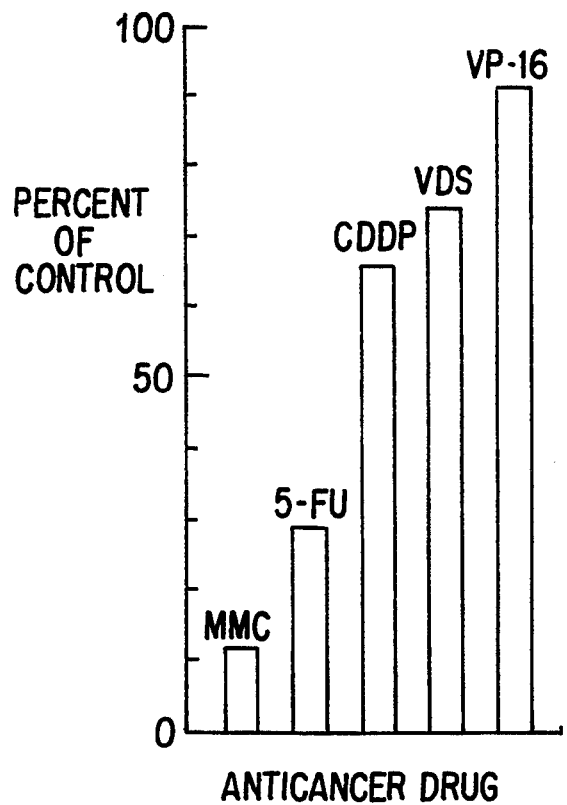
FIG. 2 is a graphic diagram which shows results obtained from the measurement of sensitivities of anticancer drugs in the examples for comparison.

When FIG. 1 showing the measurement results of the examples in this invention which comprises a combination of collagen gel culture and an image processing is compared with FIG. 2 showing the measurement results obtained from the nude mice method, an excellent correlation was obtained for all the cancer drugs. It was thus proved that the method of this invention has been highly practical as an in vitro alternative method for the in vivo nude mouse method. Furthermore, it was proved that although the nude mouse method required more than one month in period of experiment, the method of the present examples were able to provide reliable results of high accuracy within short period of time of approximately 10 days.

Figure 3:
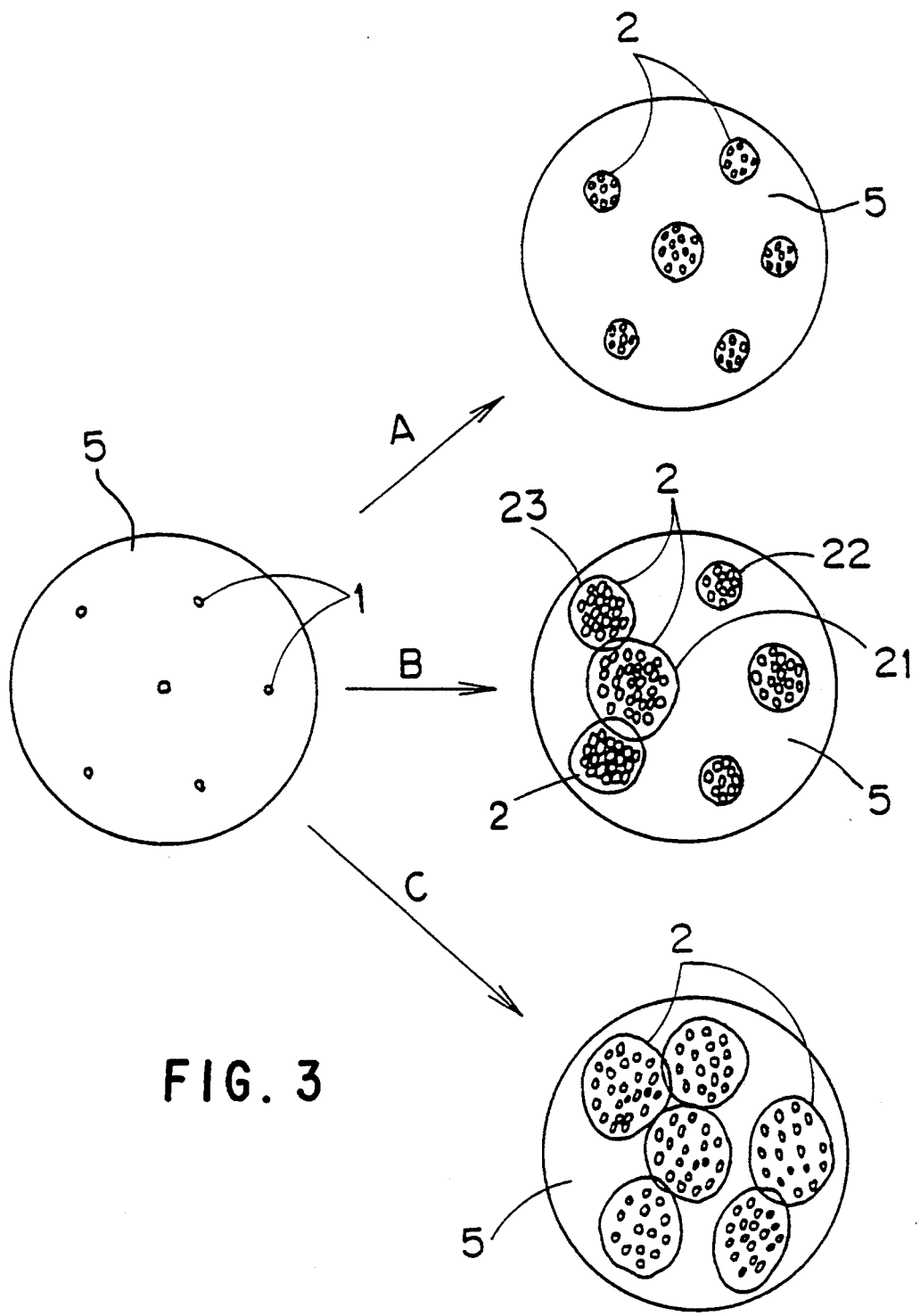
FIG. 3 is a diagram which explains three examples for proliferating extents in culturing cancer cells.

When the growth of cancer cells is measured by number-counting of colonies, an exact growth of cells is sometimes not obtained depending upon the proliferating mode of cells. For example, as seen in FIG. 3, when six pieces of single cancer cell 1 are cultured in collagen gel 5, in a case of that the growth is uniform and small as shown by the arrow A, the six colonies 2 of almost similar size are formed, so that there is no each other's overlapping of colonies. In this case the automatic counting gives a result of six for the colony number. However, in a case of that the growth is non-uniform as shown by the arrow B in FIG. 3, or in a case of that the growth is large as shown by the arrow C in FIG. 3, plural colonies 2 in a neighborhood are overlapped, so that essentially, plural colonies are determined as one by automatic counting. For example, in the proliferating case as shown by the arrow B, the automatic counting gives a result of four colonies and, in the proliferating case as shown by the arrow C, the automatic counting gives a result of two colonies (in both cases, the exact number of colonies is six). To solve an error of these kinds, there have been considered;

① a method in which the number of inoculating cells (cell density) is lowered (for example, $1 \times 10^4$ cells/ml or less); or ② a method in which measurement finishes before the colony overlapping takes place.

However, in a majority of primary cancer cells, observation of the colonies is only possible in a high density of culturing such as $5 \times 10^4$ cells/ml or more of cell density, so that according to the method ①, an exact judgment for the effects of anticancer drugs is not possible. Also, since the growth of cancer cells differs depending upon each cancer cell, the measurement in said ② method is finished before difference between the measurement and a control experiment as well as before difference in the effects of differing anticancer drugs sufficiently appears. Thus, the exact effects of anticancer drugs can not be obtained with the method ②.

Figure 4:
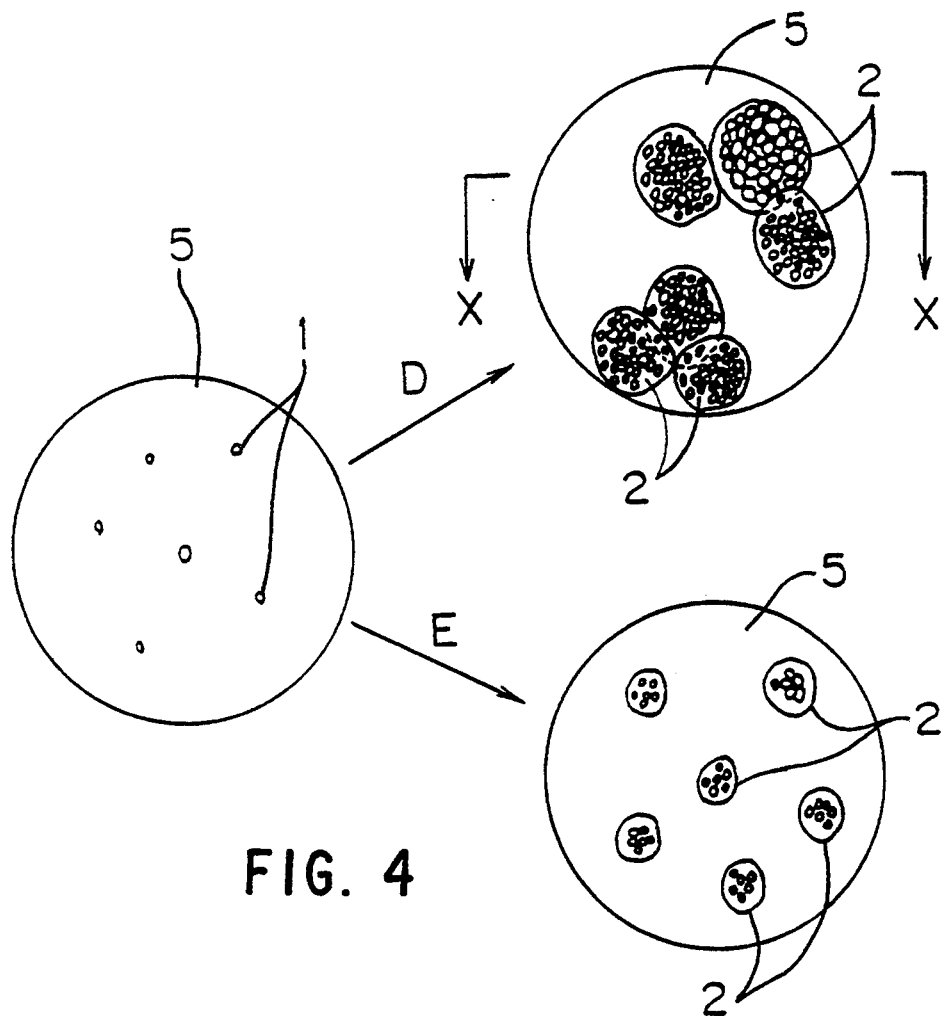
FIG. 4 is a diagram which shows, in culturing cancer cells, one example of cases where treatment with an anticancer drug was not carried out (a control experiment group) and one example of cases where the treatment was carried out.

As the forementioned, if the growth of cancer cells is not exactly measured, great inconvenience occurs in actual anticancer drug sensitivity testing methods. For example, as seen in FIG. 4, when six pieces of single cancer cell 1 are cultured in the collagen gel 5, in a case where the cancer cell is not treated with an anticancer drug as shown by the arrow D, six pieces of large colonies 2 are formed, but if three each among these colonies is each other overlapped or come in contact, the automatic counting gives a result of two for the colony number. In contrast, in a case where the cancer cell is treated with an anticancer drug as shown by the arrow E, if six pieces of small colonies 2 are formed and each other separated, the automatic counting, gives a result of six for the colony number. In general, the effect of an anticancer drug (an inhibition extent for growth) is derived from a percent ratio in the following equation:

$$\frac{\left(\begin{array}{c}\text{colony number by culturing cancer}\\ \text{cells treated with anticancer drug}\end{array}\right)}{\left(\begin{array}{c}\text{colony number of a control group}\\ \text{(by culturing cancer cells not}\\ \text{treated with anticancer drug)}\end{array}\right)} \times 100(\%)$$

and, therefore, if an anticancer drug is effective, the ratio must be less than 100%. However, in the example in FIG. 4, the ratio is 300% [(6/2)×100%].

The reason why such a unreasonable result was obtained in a case where the growth of cancer cells is measured with the number of colonies is a result of contact of colonies and/or overlapping of colonies.

Figure 5:
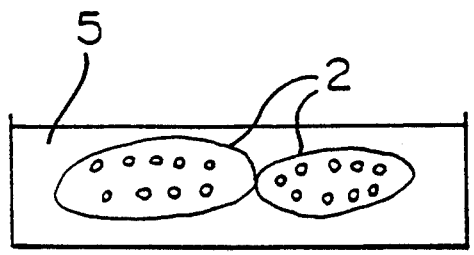
FIG. 5 is a cross-sectional view for the X—X in FIG. 4 and shows one example of cases where the colonies come in contact.

Therefore, in the present invention it is preferred to measure the growth of cancer cells by determination of the volume of colonies. In this case, the effect of an anticancer drug (an inhibiting extent for growth) is derived from a percent ratio in the following equation:

$$\frac{\left(\begin{array}{c}\text{colony volume by culturing cancer}\\ \text{cells treated with anticancer drug}\end{array}\right)}{\left(\begin{array}{c}\text{colony volume of a control group}\\ \text{(by culturing cancer cells not}\\ \text{treated with anticancer drug)}\end{array}\right)} \times 100(\%)$$

and, therefore, if an anticancer drug is effective, the ratio must be less than 100%. As seen in FIG. 5 too, neighboring colonies (for example, two pieces of colonies) 2 and 2 are each other in contact, the volume of these colonies is the same to a total volume of (two) separate colonies. In other words, in the contacting case, there is little effect or no effect on a total volume of a plural colony. Also, in a case of the overlapping, since the overlapping part is very small in volume, there is no significant effect on the total volume. Therefore, an exact measurement of the growth of cells is always possible with determination of the colony volume, but it is not always possible with determination of the colony number by an automatic counting.

As mentioned above, in measuring the growth of cancer cells with image processing, even if the growth can not be measured with determination of the colony number, exact measurement of the growth is possible with determination of an estimated colony volume. This fact was confirmed by comparison with an measured DNA amount in the following experiment. This experiment differs from said experiment in use of a human cancer cell strain not containing fibroblasts. Because of this, the measurement of the human cancer cell strain growth is exactly confirmed with measurement of the DNA amount.

EXPERIMENT 3

Culture of Cancer Cells

Using a human lung cancer cell strain, in a manner same to the control experiment in the above-mentioned example 1, a collagen gel-embedded culture was carried out without treating with an anticancer drug.

Image Processing

Picture of the human lung cancer cell strain cultured with embedding in a collagen gel substrate was, as carried out before, taken to input into the image processor as image signals. An original image inputted was, as carried out before, processed by image processing and only the image of cancer cell colonies was extracted (but in this case, since tile fibroblasts are not contained, removing-processing for them is unnecessary). Then, the colony number was counted in from the image as carried out before and, at the same time, an integrated value of the three-dimensional volume estimated from the colony image is determined. A procedure of the volume determination was carried out as follows.

1. A binary image which is a projected image of colonies is defined as an original image.

2. Separately, a picture frame capable of representing the grey level is defined as a storage-image plane.

3. The original image is copied onto the storage-image plane by setting the grey level as 1.

4. A picture element which composes a peripheral line of the projected image, is removed from the original image.

5. The projected image, which was reduced with removal of the picture elements composing the peripheral line, is defined as a new original image.

6. This new original image is copied onto the storage-image plane, to which one grey level is added.

7. The processing of 4. to 6. is repeated until the projected image disappears. By doing this, a three-dimensional image of a mountain style is obtained, in which a bottom face is a face surrounded with the peripheral line of the first projected image, and which needs not to be a real image.

8. A product of the length of a picture element with a grey level which is stored in each picture element in the storage-image plane is defined as the height.

9. The height of each picture element in the storage-image plane is integrated. With this, a volume of the three-dimensional image of a mountain style is obtained.

10. By assuming the real body of a colony as symmetrical in the surface and reverse side with respect to the projected image, a value obtained by a double of the integrated value is assigned as a volume of the colonies. Why the above assuming is carried out is due to consideration of that a form same to the form expanding broadwise in a three-dimensional culture will also expand upward and downward.

11. In cases of necessity, the outputting is carried out.

Figure 6:
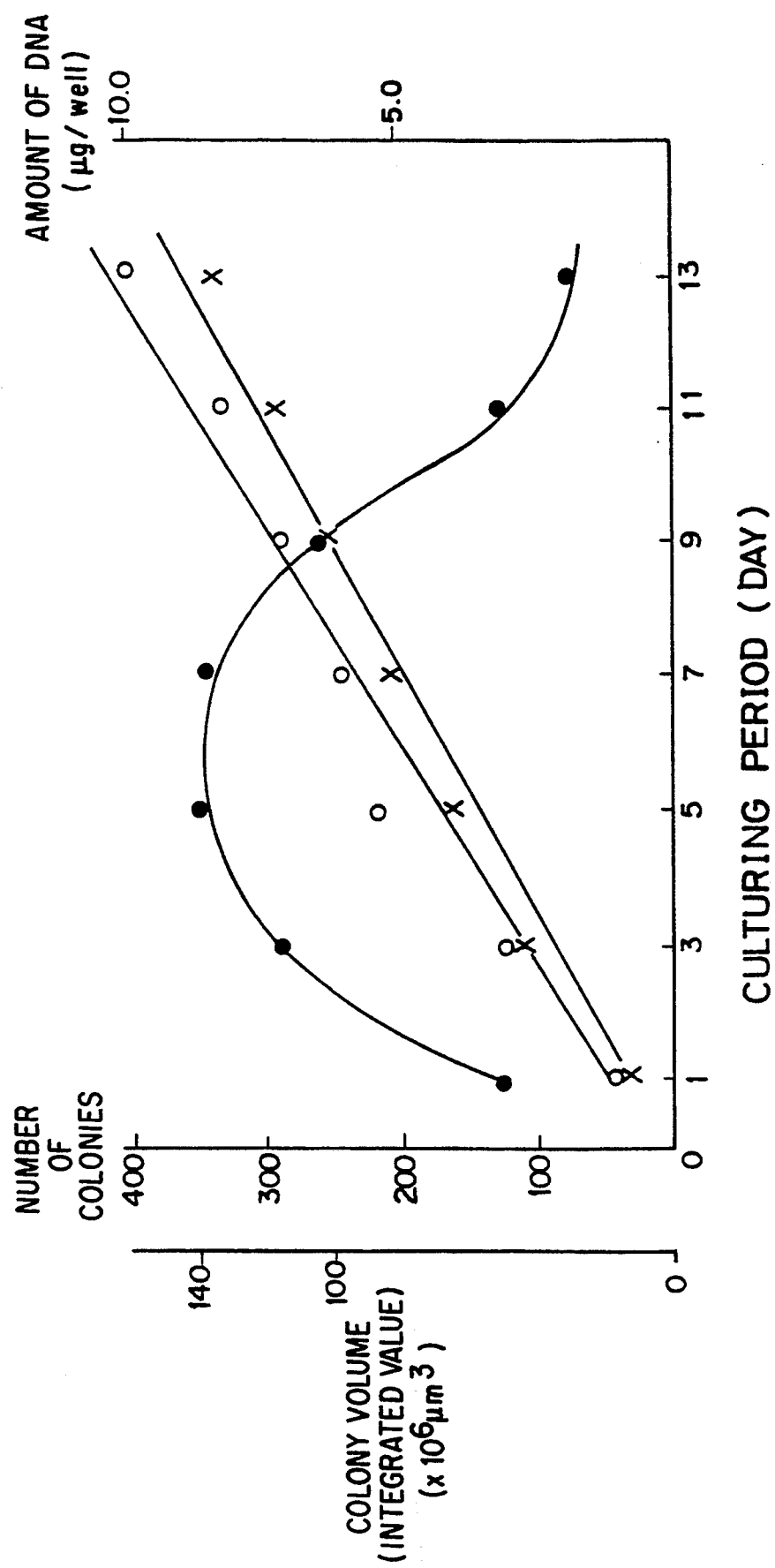
FIG. 6 is the graph which shows a correlation between the colony number and colony volume with the DNA amount.

The number and volume of colonies obtained from the above-mentioned image processing as well as the measurement results of DNA amounts are summarized in Table 3 and FIG. 6.

TABLE 3

| Culturing period (day) | 1 | 3 | 5 | 7 | 9 | 11 | 13 | 19 | 25 | Symbols in FIG. 6 |
|---|---|---|---|---|---|---|---|---|---|---|
| Number of colonies* (piece) | 126 | 287 | 347 | 343 | 256 | 124 | 69 | 45 | 39 | ● |
| Colony volume* (Integrated value) ($\times 10^6 \mu m^3$) | 14 | 44 | 67 | 82 | 97 | 116 | 134 | 205 | 235 | X |
| Amount of DNA ($\mu g$/well) | 1.04 | 2.94 | 5.29 | 6.03 | 7.26 | 8.19 | 9.77 | 13.58 | 16.21 | ○ |

(Note) *A numeral value per a 4 mm × 4 mm visual field.

As seen with the DNA amounts in the results of Table 3 and FIG. 6, the cells proliferate with a culturing period of days. Although the colony number counted is in consistent with the change in the DNA amount until the fifth day of the culturing, a peak of the colony number is observed on from the fifth to the seventh day and, after these days, a decrease is observed. This indicates that, as a result of the cell growth, the cell density becomes so high causing overlapping of cells and, therefore, an exact counting of the colony number is not achieved. On the other hand, the colony volume is well correlated with the change in the DNA amount from an initial stage of the culturing until a long period of culturing. It is thus understood that the volume-measuring method is very suitable for measuring the growth of cells, in particular, for measuring it for a long period.

Further, the number-counting measurement of colonies has the following problems. That is, the growth of cancer cells differs depending upon an individual cell(refer to the cell colonies indicated by the arrow B in FIG. 3). Since each of the colonies 21, 22, and, 23 differs in size, the number of cells contained differs, but according to number-counting of the colonies, each of the colonies 21, 22, and 23 is determined as one piece. On the other hand, in measuring the volume of colonies the colonies 21, 22, and 23 have different volume.

EXAMPLE 2

In the "Culturing of cancer cells" in the example 1, the procedure of example 1 was repeated for culturing cancer cells except that a nude mouse-xenografted human lung cancer was used instead of a nude mouse-xenografted human colon cancer,. whereby a sample obtained was processed with image processing as carried out for the example 1 in order to extract only the image of colonies.

From the image obtained, the number of colonies was counted as carried out for the example 1 and a value by integrating the volume of colonies was determined as carried out for the experiment 3.

EXAMPLE FOR COMPARISON 2

To examine the results from the example 2, by using the cells same to those used in the forementioned example 2, an anticancer drug sensitivity test by a nude mouse method is carried out in a manner same to said example for comparison 1 at the same time.

Figure 7:
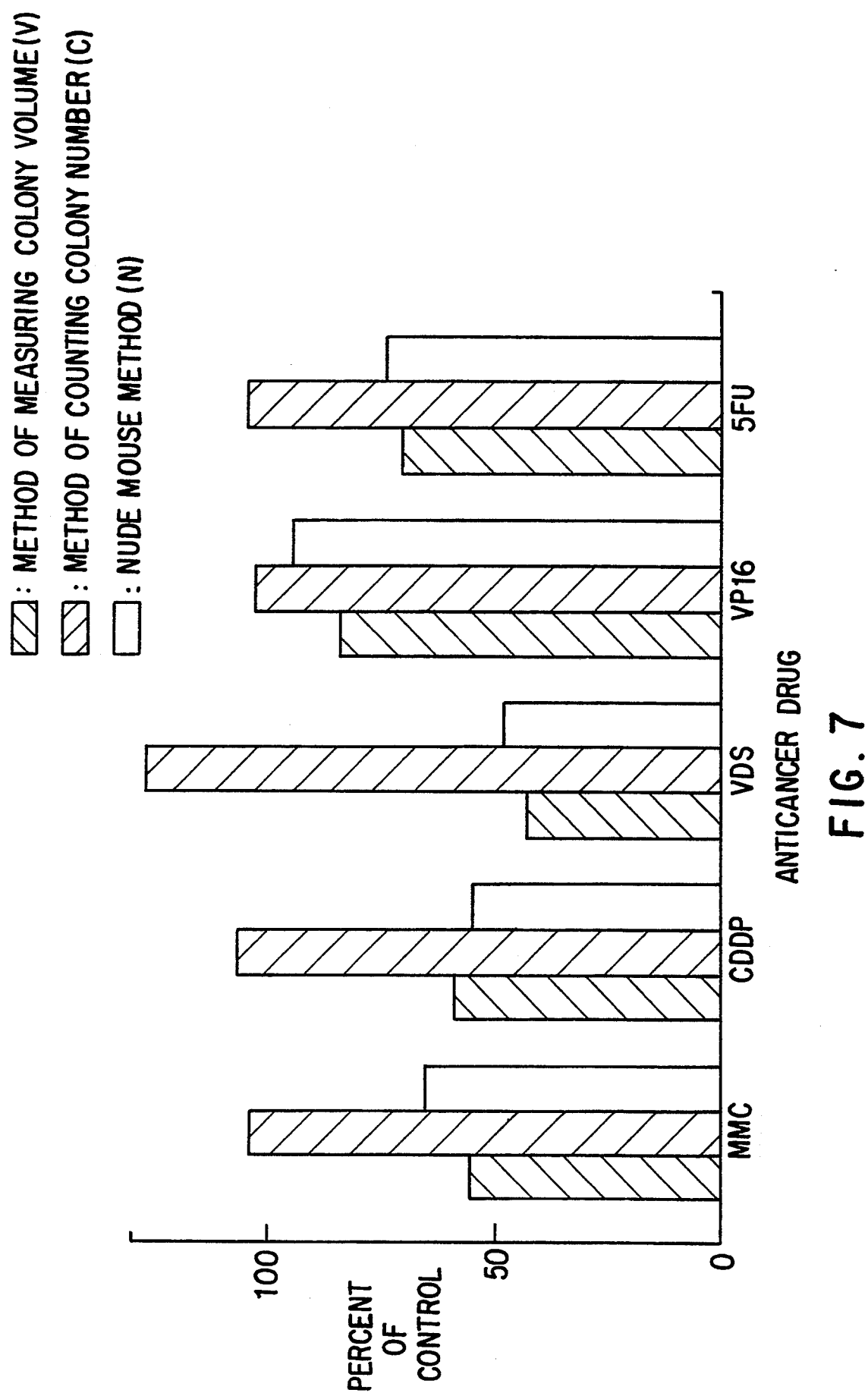
FIG. 7 is a graph which shows the sensitivity-measuring results by each anticancer drug in the example 2 and example for comparison 2.

For the results obtained from the respective examples, the percents of control were derived as carried out before and shown as the graphs in FIG. 7.

As seen in FIG. 7, a very good correlation for any anticancer drug was obtained between the results from both the nude mouse method (N) and the method of measuring colony volume (V). On the other hand, the results from the method of counting colony number (C) show abnormal values. This indicates that the cells used here show high growth and, in particular, in a case where the cells are not treated with an anticancer drug (a control experiment), the proliferating cells are overlapped as explained above so that the number-counting of colonies does not show the exact growth, while the volume-measuring of colonies shows the exact growth even in a case of this kind.

That is, in a case of actively proliferating cells or in a case where the cell density is heightened during a period of culturing, it was proved that the colony-volume measurement carried out after proliferation is an effective method for measuring the growth.

Illustration of Photographs of Monitor Television (TV) Picture Frames in Reference Photographs of monitor TV picture frames (FIGS. 8 and 9), as explained before, show the results of that the images of a sample (a control experiment), with which human cancer cells were cultured using a collagen gel substrate, were outputted onto a monitor TV at the stages of before (FIG. 8) and after (FIG. 9) the image processing. The visual scope of images is 1.4 mm in the whole width between the right and left.

Figure 8:
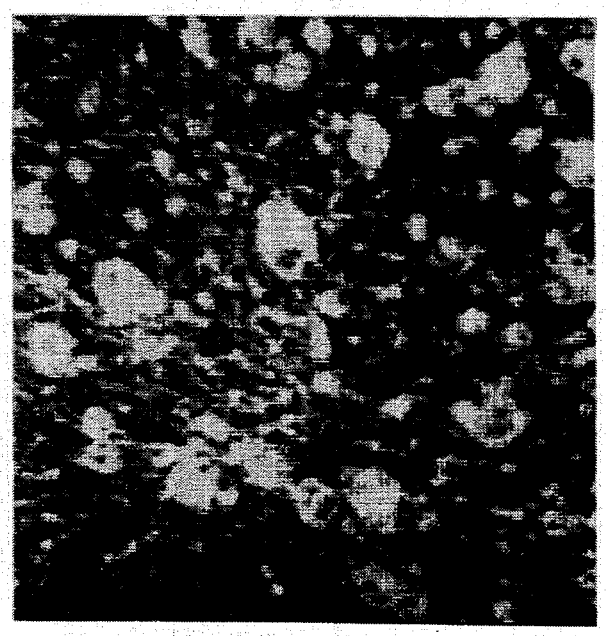
FIGS. 8–19 are photographs of monitor television pictures referred.

In the image of FIG. 8, there appears a condition under which the colonies of cancer cells having a sphere shape or a block shape and the fibroblasts having a bipolar linear shape exist in a mixing condition. The number-counting of cancer cell colonies by a nude eye so far used has been carried out under an image condition of this FIG. 8.

Figure 9:
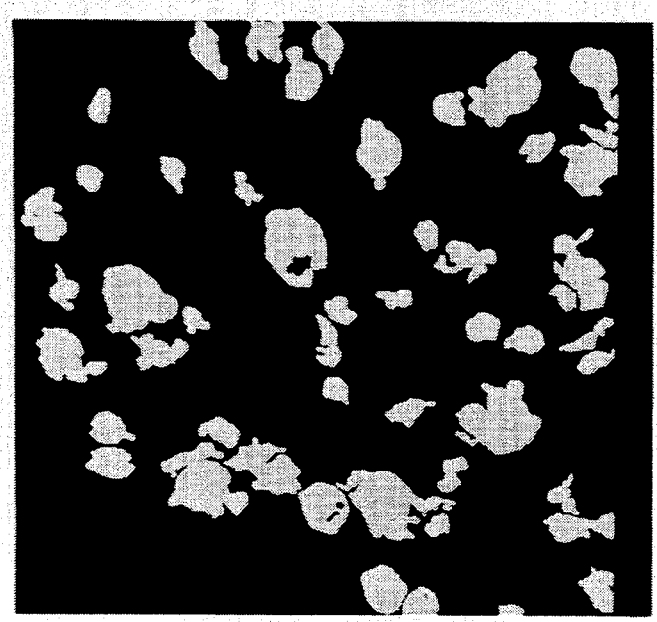
Figure 10:
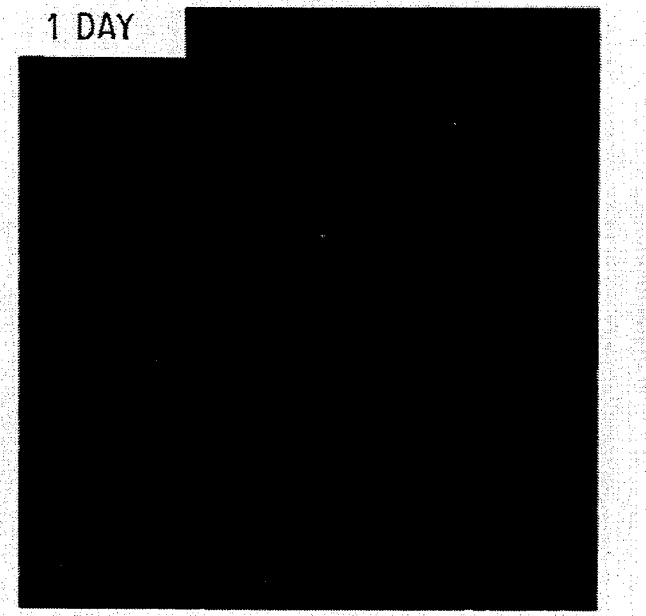
Figure 11:
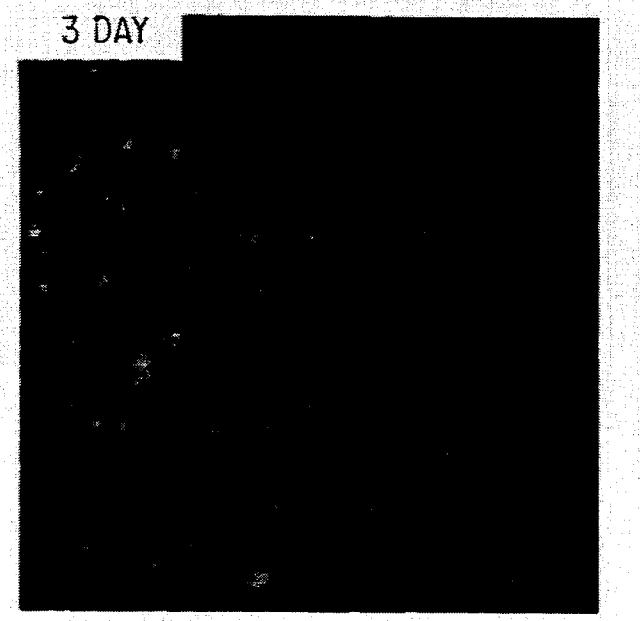
Figure 12:
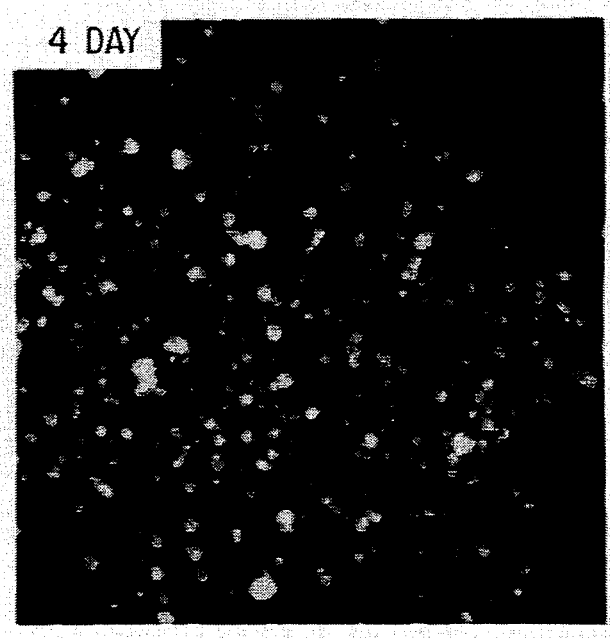
Figure 13:
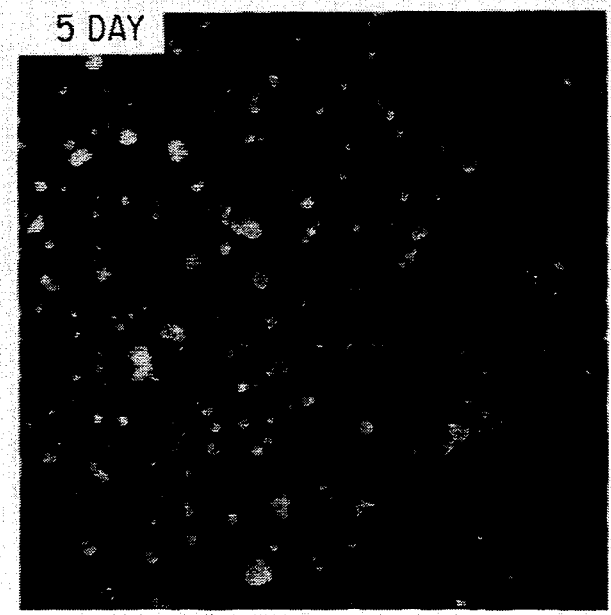
Figure 14:
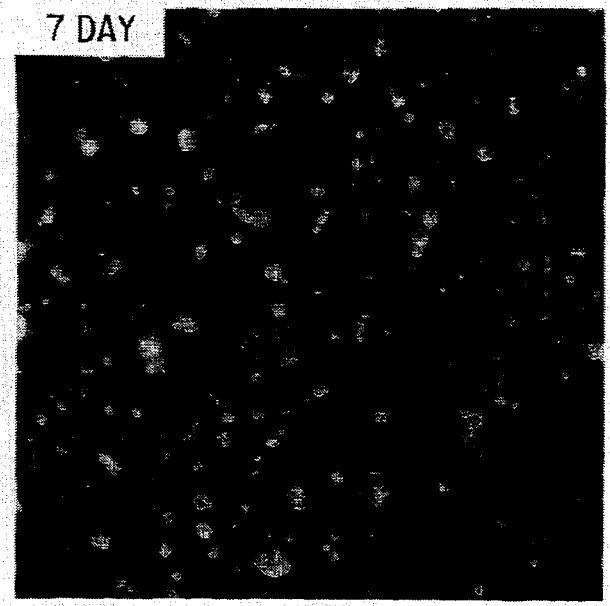
Figure 15:
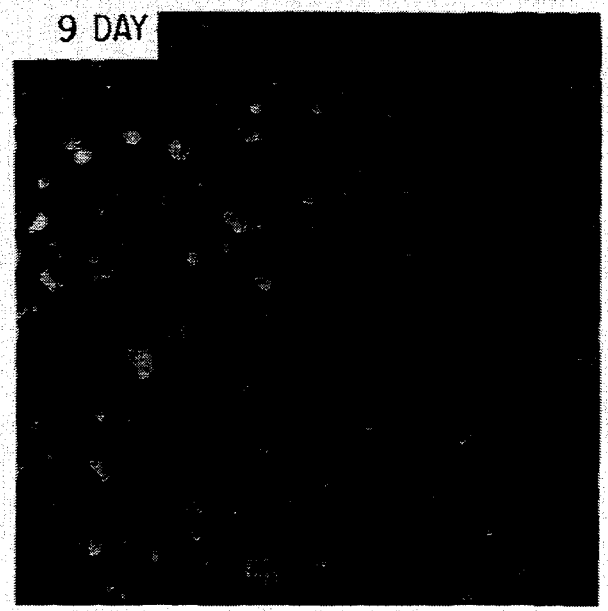
Figure 16:
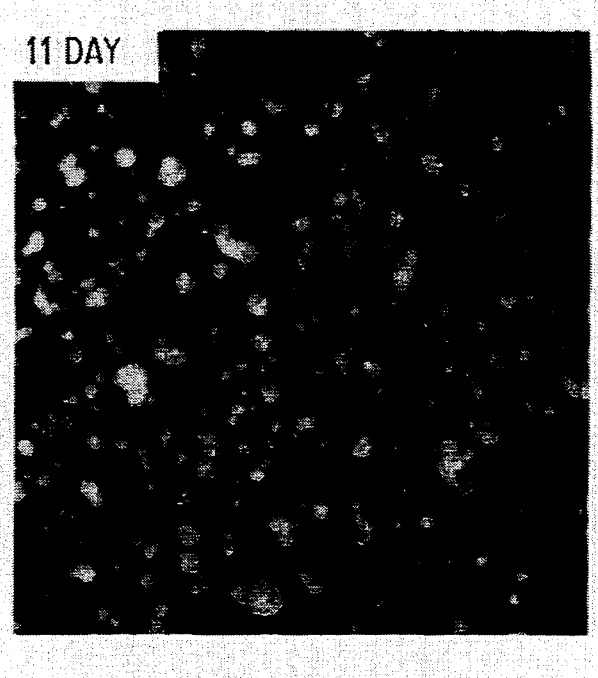
Figure 17:
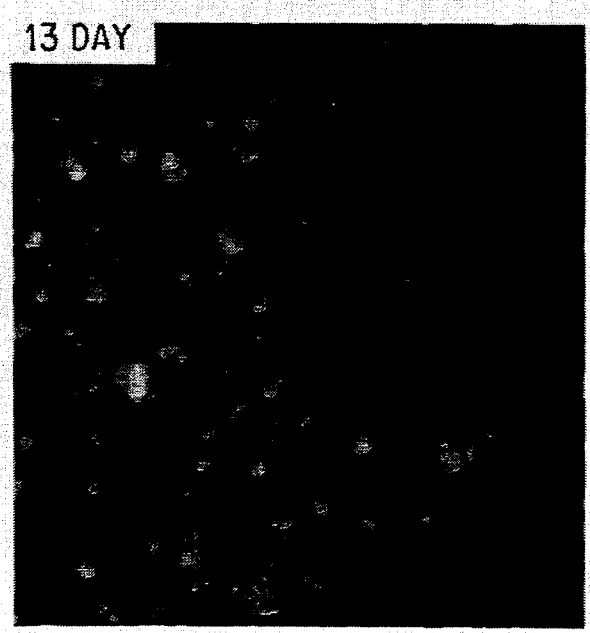
Figure 18:
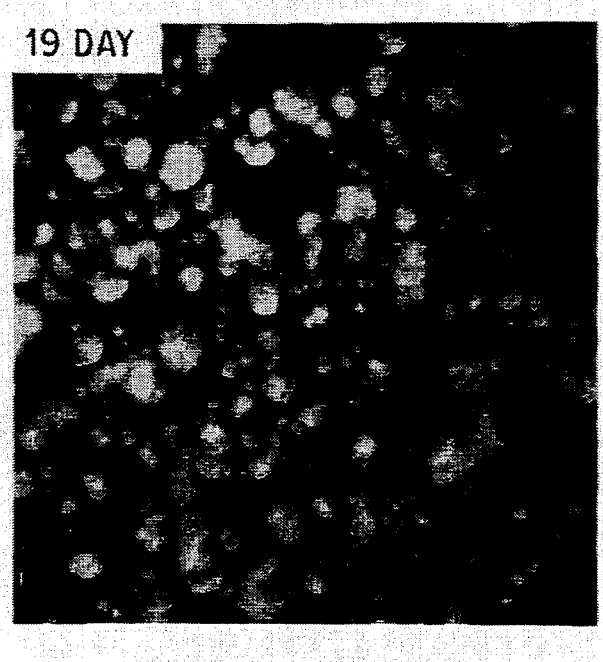
Figure 19:
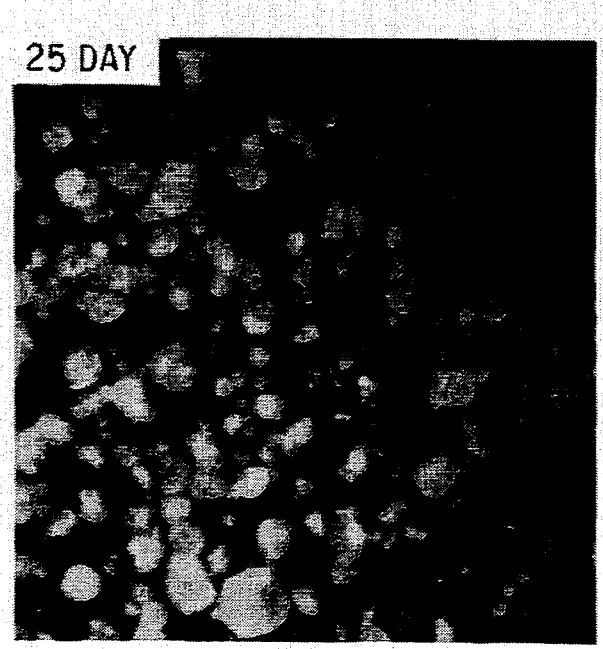

In the image of FIG. 9, there appears only the colonies of cancer cells after removing unnecessary images of fibroblasts etc. In the present invention, the colony number of cancer cells is counted by the images shown in FIG. 9.

A series of photographs, from FIG. 10 to FIG. 19, as explained before, are the photographs of picture frames obtained by that a sample (control) is given by culturing human lung cancer cells with embedding them by using a collagen gel substrate, culturing conditions of the sample varying with the passage of culturing days are processed by image processing, and the images thus-obtained are outputted onto a monitor TV. The visual scope of images is 4 mm in the whole width between the right and left.

The photographs from FIG. 10 to FIG. 19 are the images, each of which is obtained in sequence with the passage of following culturing days; one day, three days, four days, five days, seven days, eleven days, thirteen days, nineteen days, and twenty-five days. The cancer cell colonies which are shown with a white or bluish gray color are gradually varying from a small spot type to a large block type and one another coming in contact or overlapping. The growth is not uniform and differs with an individual cell. In the present invention the growth of cancer cells is measured by the colony number or colony volume, for example, with the, images which are shown in anyone of Photographs from FIG. 10 to FIG. 19. Beside, as the forementioned, it is possible to trace the growth with the passage of culturing periods of days.

According to the forementioned anticancer drug sensitivity-testing method in the present invention, since a collagen gel is used as a substrate for culturing cancer cells, a variety of cancer cells of such kinds that the culturing is impossible in hitherto-known soft agar substrate and the like can be cultured.

The effects of fibroblasts etc., which proliferate together with cancer cells in a case where the cancer cells are cultured in the collagen gel substrate, can be eliminated by measuring the growth of cancer cells by image processing, so that the testing results are obtained accurately and quickly.

In the image processing of the growth of cancer cells, the measurement of colony volume gives more reliable results than the counting of the colony number, and gives results of the growth for a longer period.

With the results forementioned, it can be said that a sensitivity-testing method useful for development of anticancer drugs is provided which, compared with a testing method so far used, has much wider applicability for many kinds of cancer cells, is much simpler in handling, and is capable of providing the test results promptly and accurately.

What is claimed is:

1. A method for testing the sensitivity of anticancer drugs comprising the steps of:
   (a) proliferating cancer cells in a collagen gel substrate after contacting the cells with an anticancer drug, wherein fibroblast cells which are contained in cancer tissues proliferate together with the cancer cells of step (a),
   (b) proliferating cancer cells for a control in a collagen gel substrate without contacting with the anticancer drug, wherein fibroblast cells which are contained in cancer tissues proliferate together with the cancer cells of step (b),
   (c) obtaining a picture image for the cancer cells of step (a) and a control picture image for the cancer cells of step (b), each picture image comprising first images of proliferated cancer cells and colonies composed of the proliferated cancer cells, and second images of proliferated fibroblast cells, and
   (d) measuring the growth of the cancer cells proliferated in said substrates of step (a) and step (b) by:
      (1) inputting both picture images after growth into an image processor,
      (2) selectively extracting the first images, respectively, from said both picture images using the image processor, and
      (3) determining the colony count or volume of said cancer cells using the image processor and using the selectively extracted first images from said picture image for the cancer cells of step (a) and the selectively extracted first picture images from said control picture image for the cancer cells of step (b) to compare the colony count or volume of the cancer cells of step (a) with the colony count or volume of the cancer cells of step (b).

2. The method as claimed in claim 1, wherein the step of selectively extracting the first images using the image processor comprises the steps of:
   (a) digitizing the picture image into picture elements,
   (b) converting into numerals, the concentrations of each picture element of the digitized picture image,
   (c) selecting, according to a value of said numerals, the objects to be processed,
   (d) processing said objects on the basis of at least one of the differences in shape and said value of said numerals to remove the second images from said digitized picture image.

3. The method as claimed in claim 2, wherein the numerals refer to gray levels of said picture elements.

4. The method as claimed in claim 3, wherein the measurement of the growth of the cancer cells is determined by counting the number of said first images.

5. The method as claimed in claim 3, wherein the measurement of the growth of the cancer cells is carried out by calculating the total volume of said selectively extracted first images using the image processor.

6. The method as claimed in claim 5, wherein the calculation of the total volume of the selectively extracted first images using the image processor comprises the steps of:
   (a) providing binary images of the selectively extracted first images,
   (b) processing said binary images to form the corresponding three-dimensional images of a mountain style of which the bottom face is a face surrounded with the peripheral line of each of said binary images by:
      (1) providing a storage-image plane to represent a gray level,
      (2) copying said binary images onto the storage-image plane, the copied binary images having a gray level of 1,
      (3) removing the picture elements forming the peripheral lines of said binary images from the binary images to form reduced binary images,
      (4) providing the reduced binary images of step (3) in place of said binary images,
      (5) copying the reduced binary images of step (3) over the corresponding copied binary images of step (2) on said storage-image plane to form stored images, the copied, reduced binary images having a gray level of 1, and
      (6) repeating steps (3), (4) and (5) until said reduced binary images disappear, so that said stored images form said corresponding three-dimensional images of a mountain style, and
   (c) calculating the total volume of the selectively extracted first images by:
      (1) providing, as a height, the product of the length of a picture element with the corresponding gray level stored on each picture element on the storage-image plane,
      (2) integrating the height on each picture element to obtain the volume of each three-dimensional image of a mountain style, and multiplying the volume by two to obtain the total volume of said first images.

* * * * *